US011565250B2

(12) United States Patent
Gaio et al.

(10) Patent No.: US 11,565,250 B2
(45) Date of Patent: Jan. 31, 2023

(54) VERSATILE 3D STRETCHABLE MICRO-ENVIRONMENT FOR ORGAN-ON-CHIP DEVICES FABRICATED WITH STANDARD SILICON TECHNOLOGY

(71) Applicant: Biond Solutions B.V., Delft (NL)

(72) Inventors: Nikolas Gaio, Delft (NL); William Quiros Solano, Delft (NL)

(73) Assignee: BIOND SOLUTIONS B.V., Delft (NL)

( * ) Notice: Subject to any disclaimer, the term of this patent is extended or adjusted under 35 U.S.C. 154(b) by 132 days.

(21) Appl. No.: 16/320,928

(22) PCT Filed: Jul. 20, 2017

(86) PCT No.: PCT/NL2017/050492
§ 371 (c)(1),
(2) Date: Jan. 25, 2019

(87) PCT Pub. No.: WO2018/021906
PCT Pub. Date: Feb. 1, 2018

(65) Prior Publication Data
US 2019/0168218 A1    Jun. 6, 2019

(30) Foreign Application Priority Data
Jul. 25, 2016 (NL) .................................... 2017227

(51) Int. Cl.
*B01L 3/00*         (2006.01)
*C12M 3/06*        (2006.01)
*C12M 1/00*        (2006.01)
(52) U.S. Cl.
CPC ... *B01L 3/502707* (2013.01); *B01L 3/502715* (2013.01); *C12M 23/16* (2013.01);
(Continued)

(58) Field of Classification Search
CPC ......... B01L 3/502707; B01L 3/502715; B01L 2200/12; B01L 2300/0645;
(Continued)

(56) References Cited
U.S. PATENT DOCUMENTS 8,383,060 B2 * 2/2013 Dekker ................... H01L 37/00
422/502
2003/0160538 A1 * 8/2003 Tomonari ............... H02N 10/00
310/307
(Continued)

FOREIGN PATENT DOCUMENTS

JP   2015099031 A   5/2015
WO   2015/138034     9/2015
(Continued)

OTHER PUBLICATIONS

Van Meer, B. J. "Design of Cytostretch Skin A human cell based stretchable, flexible and mass-producible skin tissue model for drug development." (2014). (Year: 2014).*
(Continued)

*Primary Examiner* — Jennifer Wecker
*Assistant Examiner* — Oyeleye Alexander Alabi
(74) *Attorney, Agent, or Firm* — Peacock Law P.C.; Justin Muehlmeyer

(57) ABSTRACT

The present invention is in the field of microfluidic devices produced with silicon technology wherein at least one 3D microenvironment is present, a method of producing said device using silicon based technology, and a use of said device in various applications, typically a biological cell experiment, such as a cell or organ on a chip experiment, and use o the device as a microreactor.

20 Claims, 8 Drawing Sheets

(52) U.S. Cl.
CPC ............ *C12M 23/20* (2013.01); *C12M 23/22* (2013.01); *B01L 2200/12* (2013.01); *B01L 2300/0645* (2013.01); *B01L 2300/0663* (2013.01); *B01L 2300/0887* (2013.01); *B01L 2300/0893* (2013.01); *B01L 2300/123* (2013.01); *B01L 2300/1822* (2013.01); *B01L 2300/1827* (2013.01)

(58) Field of Classification Search
CPC ..... B01L 2300/0663; B01L 2300/0887; B01L 2300/0893; B01L 2300/123; B01L 2300/1822; B01L 2300/1827; C12M 23/16; C12M 23/22
See application file for complete search history.

(56) References Cited

U.S. PATENT DOCUMENTS

| | | | |
|---|---|---|---|
| 2004/0045891 A1 | | 3/2004 | Gilbert et al. |
| 2006/0154361 A1 | | 7/2006 | Wikswo et al. |
| 2009/0131858 A1 | | 5/2009 | Fissell et al. |
| 2010/0230613 A1* | | 9/2010 | Pieprzyk ............... C12Q 1/686 250/459.1 |
| 2013/0137132 A1* | | 5/2013 | Dekker ................. D06F 75/22 435/29 |

FOREIGN PATENT DOCUMENTS

| | | | | |
|---|---|---|---|---|
| WO | WO-2015138034 A2 * | 9/2015 | ............ | C12M 23/16 |
| WO | 2016/004394 | 1/2016 | | |
| WO | 2016/010861 | 1/2016 | | |
| WO | 2016/049363 | 3/2016 | | |
| WO | 2016/049365 | 3/2016 | | |
| WO | WO-2016049363 A1 * | 3/2016 | ........ | B01L 3/502715 |
| WO | 2018/012906 | 2/2018 | | |

OTHER PUBLICATIONS

Booth, Ross, et al., "Characterization of a microfluidic in vitro model of the blood-brain barrier (mBBB)", Lab on a Chip, Issue 10, https://pubs.rsc.org/en/content/articlelanding/2012/lc/c2lc40094d/unauth#!divAbstract, 2012, 1-2.

Gaio, Nikolas, et al., "Cytostretch, an Organ-on-Chip Platform", Micromachines, vol. 7, No. 120, 2016, 1-14.

Huh, Dongeun, et al., "Microfabrication of human organs-on-chips", Nature Protocols. vol. 8, No. 11, 2013, 2135-2157.

Huh, Dongeun, et al., "Reconstituting Organ-Level Lung Functions on a Chip", Science, vol. 328, Issue 5986, 2010, 1662-1668.

Jang, Kyung-Jin, et al., "A multi-layer microfluidic device for efficient culture and analysis of renal tubular cells", Lab on a Chip, vol. 10, No. 1, 2010, 36-42.

Kim, Hyun Jung, "Human gut-on-a-chip inhabited by microbial flora that experiences intestinal peristalsis-like motions and flow", Lab on a Chip, Issue 12, 2012, 2165-2174.

Kloter, U., et al., "High-Resolution Patterning and Transfer of Thin Pdms Films: Fabrication of Hybrid Self-Sealing 3DMicrofluidic Systems", Proceedings of the 17th IEEE International Conference on Micro Electro Mechanical Systems (MEMS): Maastricht, Netherlands, 2004, 745-748.

Regehr, Keil J., et al., "Biological implications of polydimethylsiloxane-based microfluidic cell culture", Lab Chip., vol. 9, No. 15, 2009, 2132-2139.

\* cited by examiner

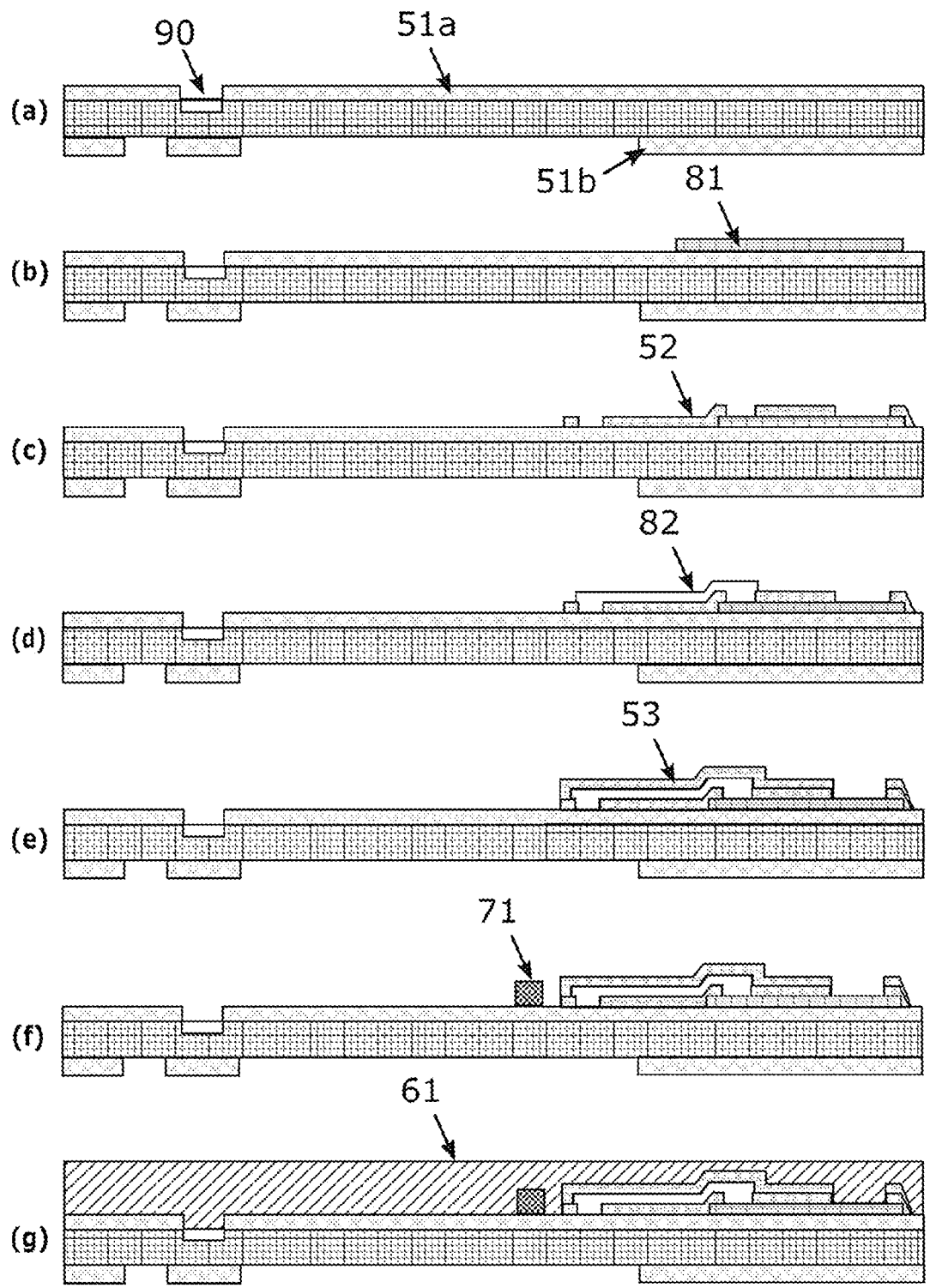
Fig. 1a-g

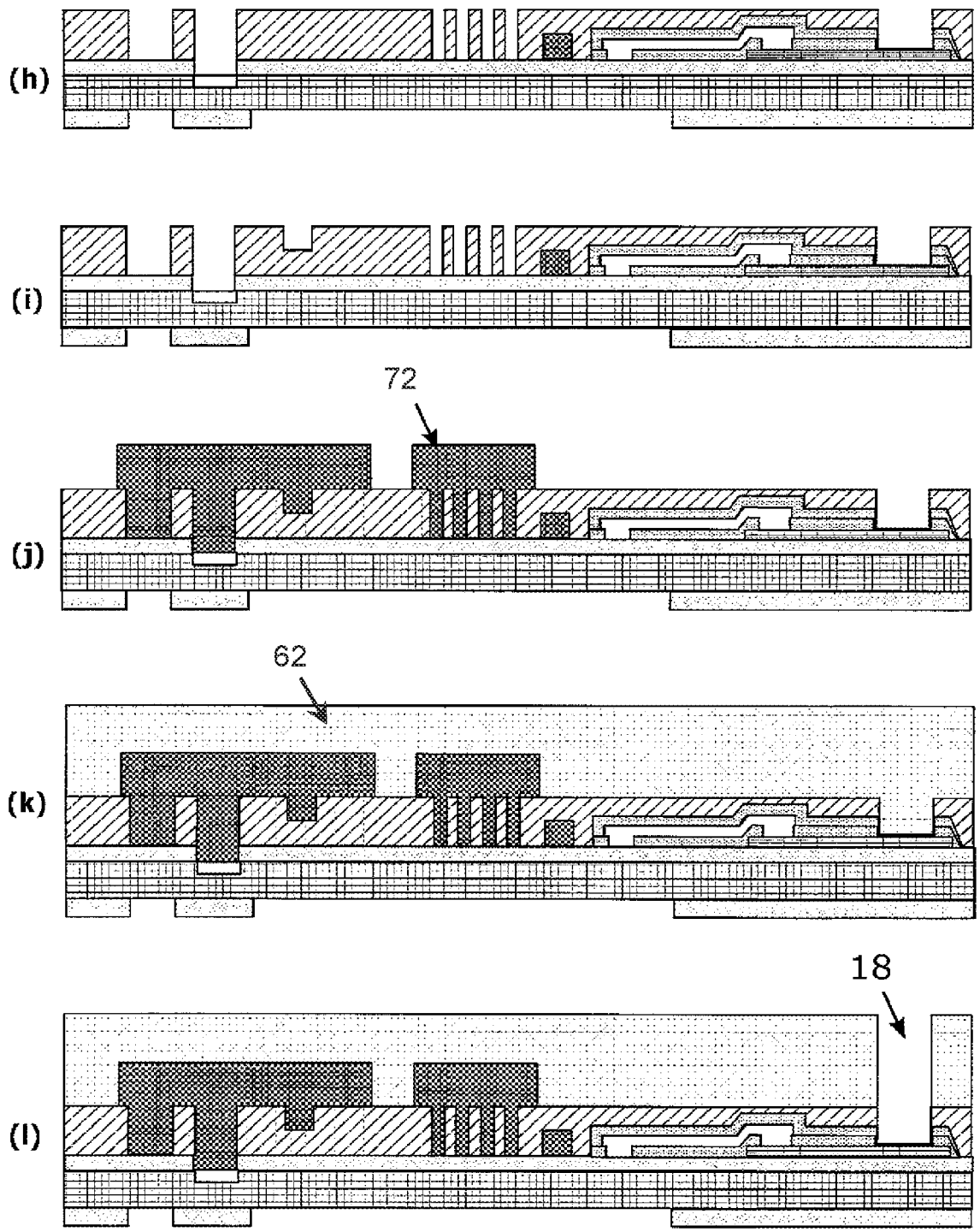
Fig. 1h-l

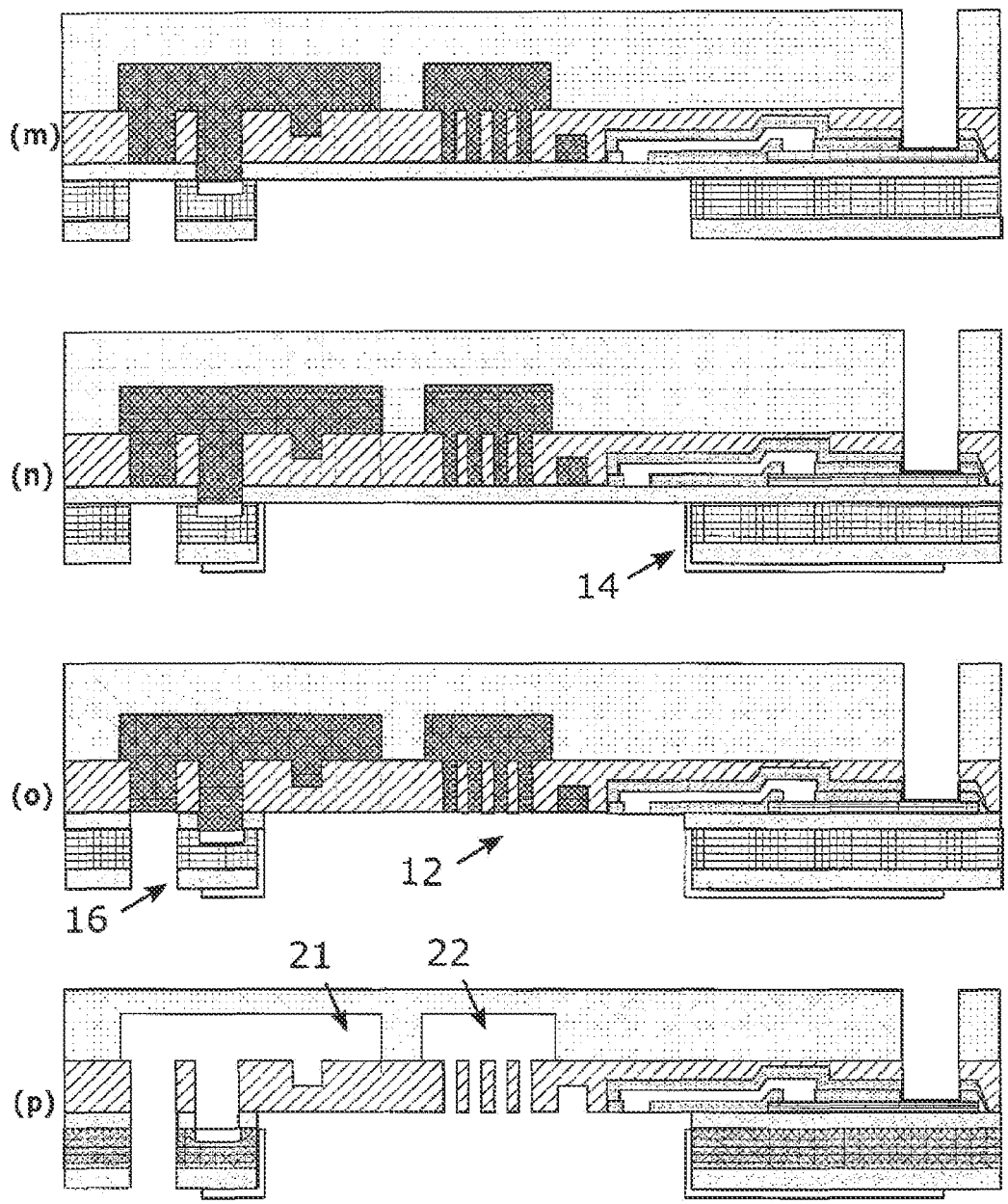
Fig. 1m-p

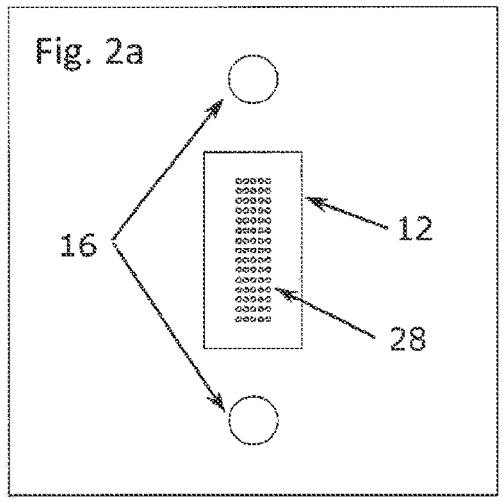
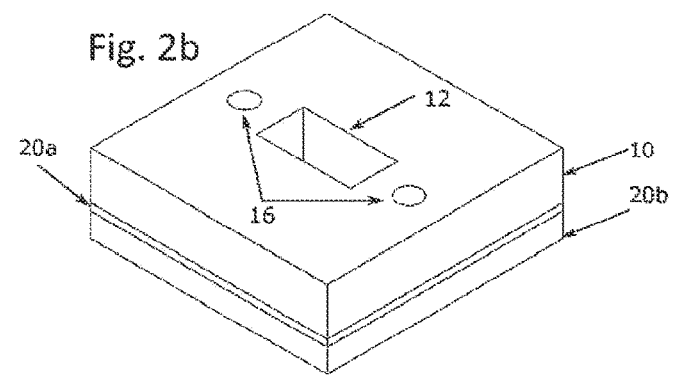
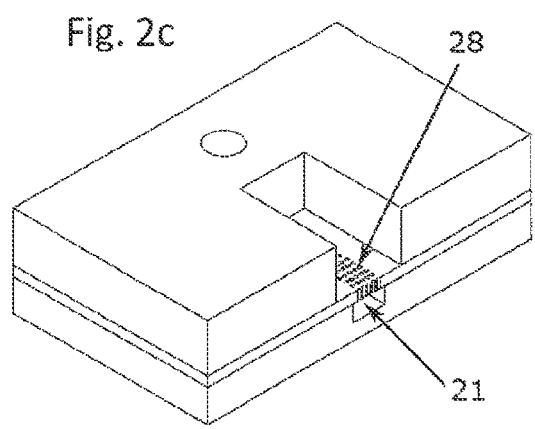
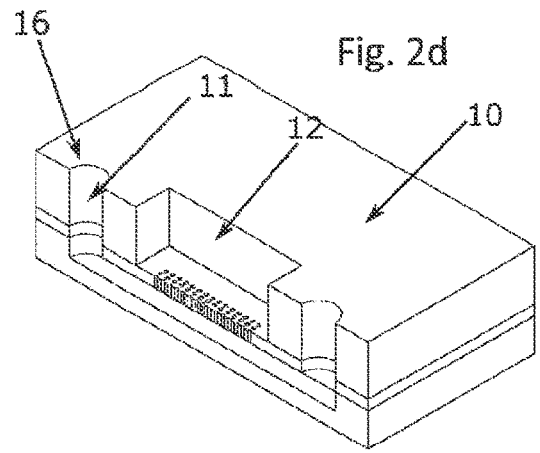
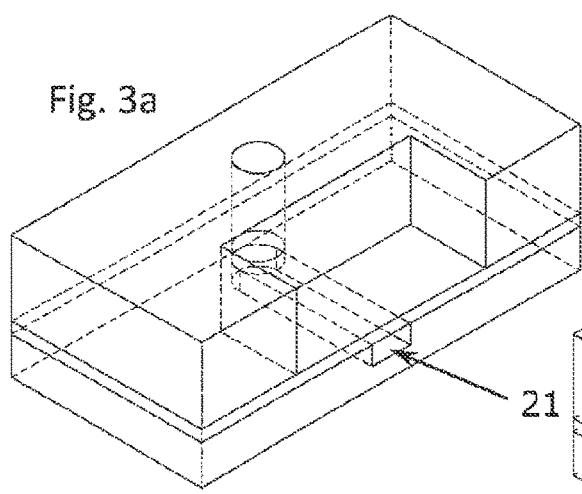
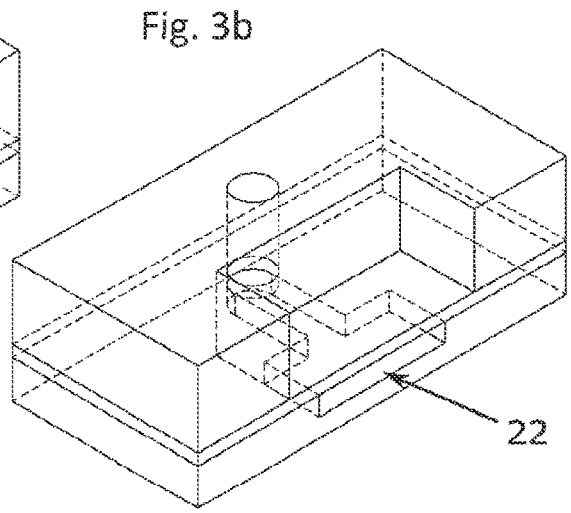

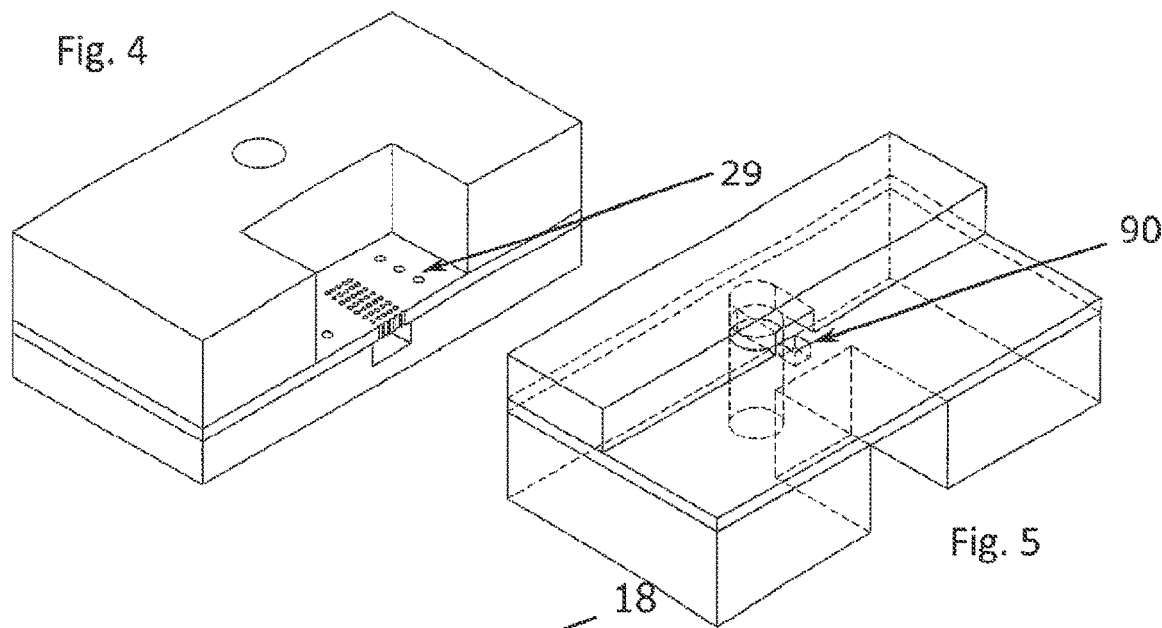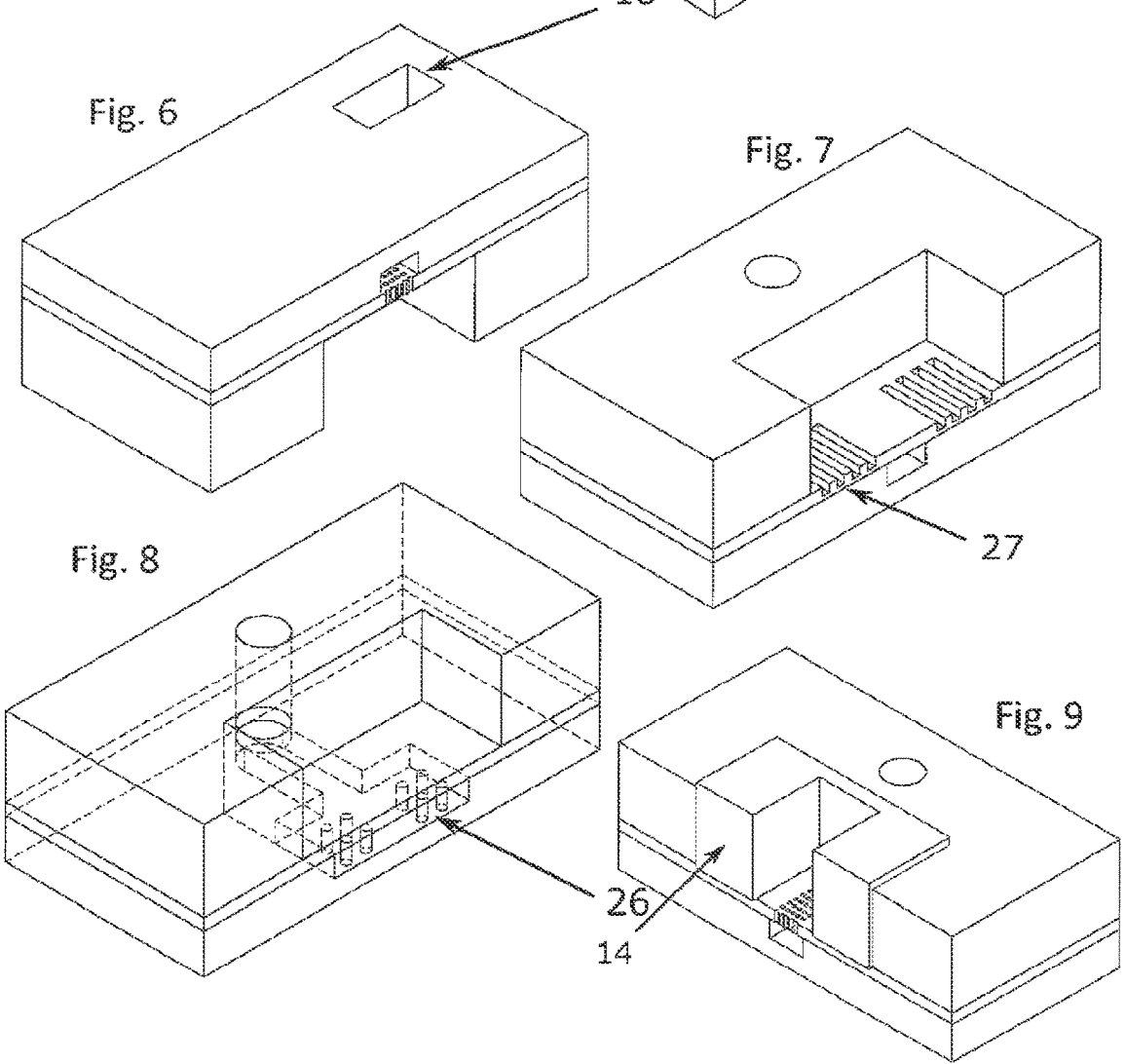

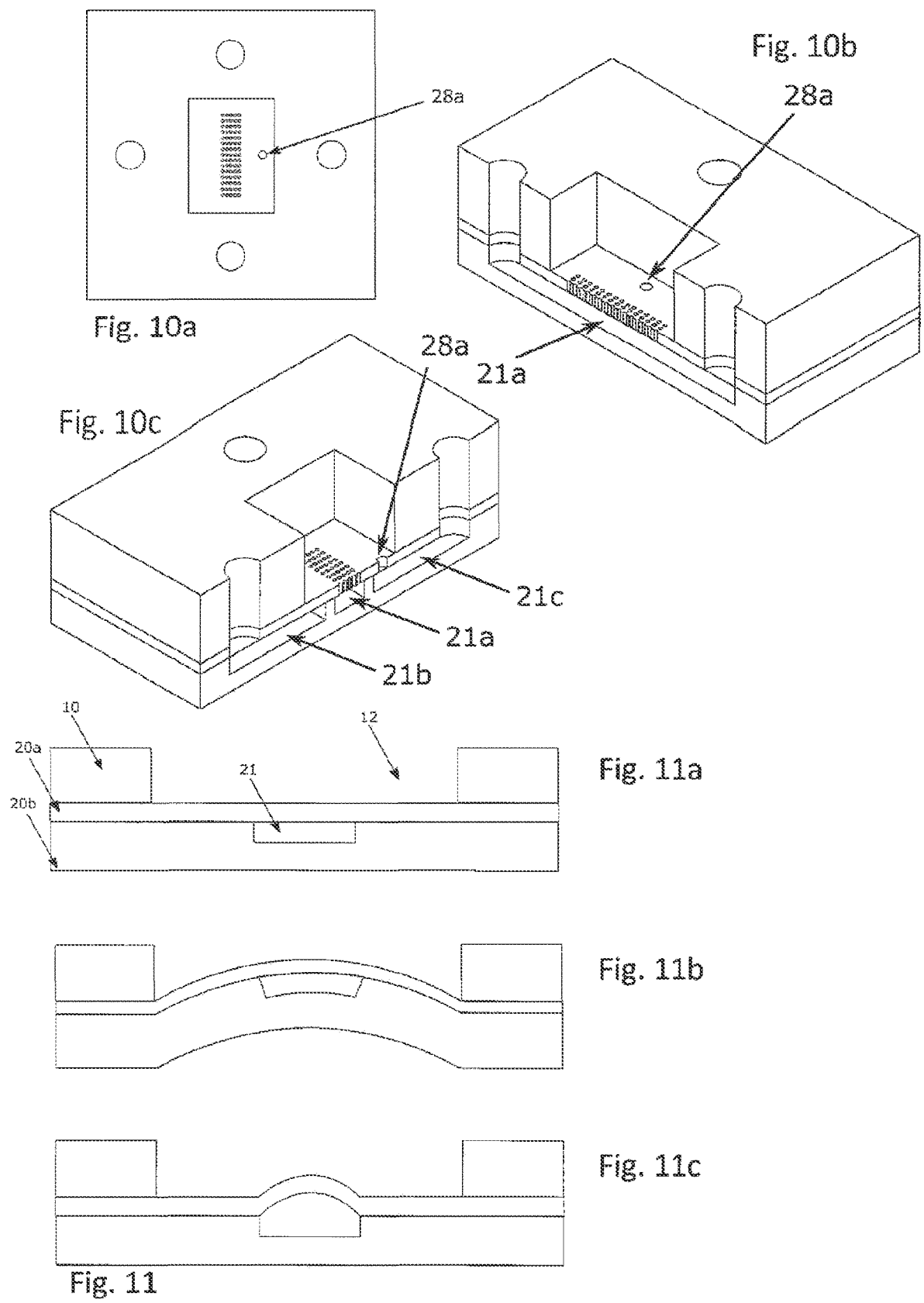

VERSATILE 3D STRETCHABLE MICRO-ENVIRONMENT FOR ORGAN-ON-CHIP DEVICES FABRICATED WITH STANDARD SILICON TECHNOLOGY

FIELD OF THE INVENTION

The present invention is in the field of microfluidic devices produced with silicon technology wherein at least one 3D microenvironment is present, a method of producing said device using silicon based technology, and a use of said device in various applications, typically a biological cell experiment, such as a cell or organ-on-a-chip experiment, and lab-on-a-chip experiment, and use of the device as a micro-reactor.

BACKGROUND OF THE INVENTION

A microfluidic device relate to a set of technologies with an aim to manipulate at least one small fluid (liquid or gas) volume within microsystems produced by human beings. In the device a cell culture or an individual cell or the like may be present. An experiment on said cell culture refers to the maintenance and growth of cells in a well-controlled environment. The environment may resemble naturally occurring circumstances. As such a cell can likewise be studied under application of at least one of numerous signals that might be present in their naturally occurring surrounding microenvironment.

A microfluidic cell culture may attempt to manipulate cells, such as by culturing, maintaining, and growing, and qualitatively and quantitatively experimenting and analyzing cells in microfluidic volumes. Such may relate to an attempt to understand a cell culture, such as a stem cell culture, non-dividing or slowly dividing cells, e.g. in terms of an interaction between cell culture parameters and the micro environmental conditions created by microfluidic devices. It is considered that dimensions of the microfluidics, such as chamber and channels, are well suited to the physical scale of the biological cells and other applications.

In general it is considered that microfluidics provide a good degree control over e.g. cell culture conditions. Typically a movement of fluids in the microfluidics is considered to be laminar; a fluid volume is typically in the order of $10^{-6}$-$10^{-12}$ l; fluid flow may be controlled precisely in terms of volume and timing, such as by providing an in-chip valve; also precise chemical and physical control of the microenvironment is possible; a production of a multitude of individually controllable cell culture chambers on a single device is considered, albeit typical prior art technologies rely on manual procedures which are considered to be insufficiently controlled.

Some prior art documents recite microfluidic devices. WO2016/049363 A1, WO2016/049365 A1, WO2016/010861 A1, WO2016/004394 A1, and US15/2955534 A1 recite relatively simple organ on chip devices, which cannot include any complex sensing/stimulation elements; hence these device are not unsuited for most applications.

Huh, Dongeun, et al. In "Reconstituting organ-level lung functions on a chip." Science 328.5986 (2010): 1662-1668, Kim, Hyun Jung, et al. in "Human gut-on-a-chip inhabited by microbial flora that experiences intestinal peristalsis-like motions and flow." Lab on a Chip 12.12 (2012): 2165-2174, Huh, Dongeun, et al. in "Microfabrication of human organs-on-chips." Nature protocols 8.11 (2013): 2135-2157, and WO2015/138034 A1 present devices that have a limited production yield, limited throughput and limited functionality and do not seem to relate to more than a specific microfluidic device; the devices are considered to provide some basic functionality but are not ready in technological terms for further application.

Recently one of the present inventors published an article (Gaio et al., "Cytostretch, an Organ-on-Chip Platform", Micromachines, Vol. 7, Jul. 14, 2016, 120 (p. 1-14). The Cytostretch device does not relate to a microfluidic channel. It is a foil that does not have any channel. For fabrication some steps overlap with the present method, but the above patent WO2015/138034 A1 and this paper do not relate to e.g. a channel in a thin layer.

The present invention relates to a device and a method of producing said device which overcomes one or more of the above or further disadvantages, without jeopardizing functionality and advantages.

SUMMARY OF THE INVENTION

The present invention relates in a first aspect to a device according to claim 1, which has amongst others the advantages of a higher throughput, being cheaper to produce, being more reliable and more versatile, providing a better handling of e.g. cells, and providing a wider functionality. For an organ-on-Chip the present device improves disease modelling, drug screening and toxicity tests. Pharmaceutical companies may use this as a tool to partially replace animal testing improving animal welfare and drug testing reliability.

The present device comprises at least three distinct layer in which microfluidic and nano-/microscale elements and the like are provided. The first two layers are made of a polymer, typically but not necessarily the same polymer for both layers; a first polymer layer 20a is provided on a substrate, typically silicon 10 or a glass wafer, and is relatively thin; for the purpose of the invention the terms "substrate", "silicon", and "glass" are considered interchangeable; the top layer may be considered to relate to a membrane, also referred to as a foil, which is considered to relate to a selective barrier; in addition or in alternative, the present polymer layers may be considered to relate to a film, i.e. a thin continuous polymeric material, whereas a thicker plastic material would relate to a sheet; the top layer preferably is provided with a matrix of holes 28 therein, the at least one hole allowing passage of e.g. fluids, gases, species, micro-particles, ions, etc. which can be adapted for specific uses; the top layer has a thickness of 0.05-30 µm, preferably 0.1-25 µm, more preferably 0.2-20 µm, even more preferably 0.5-8 µm thin, such as 1-5 µm or 2-3 µm; the top layer is optically transparent, or at least largely transparent, in order to use a microscope to view samples, such as biological cells, such as >90% transparent e.g. >98%; in contact with the relative thin polymer layer 20a is a thicker polymer bottom layer 20b; the bottom layer comprises at least one second micro-channel 21 and/or at least one second micro-chamber 22 at least partly embedded in the polymer bottom layer; the number, layout, sizes, and further characteristics of these microfluidics can be adapted for specific uses; the microfluidics may be embedded fully in the bottom layer 20b and/or may be embedded partly, such as in the case of a well; the polymer bottom layer is thicker than the top layer and preferably has a thickness of 50-2000 µm, hence is at least one order of magnitude thicker than the top layer, and typically 2-3 orders of magnitude thicker; the thickness is preferably 150-1000 µm, more preferably 200-500 µm, even more preferably 250-400 µm, such as 300-350 µm; the device further comprises silicon based microfluidics in microfluidic contact with the top layer 20a of the polymer based microfluidics wherein the silicon based microfluidics are accessible and/or can be made accessible for use of the device; the substrate, e.g. silicon, based microfluidics comprise at least one first micro-channel 11 and/or at least one first micro-chamber 12 at least partly embedded (see above) in the silicon, and at least one input 16, wherein the input 16 is in microfluidic contact with the at least one second micro-channel 21 and/or at least one second micro-chamber 22 embedded in the polymer bottom layer, e.g. as functionally defined or required; the support or substrate 10 may relate to a typically used wafer in a silicon semiconductor process such as of Si or glass; wherever silicon is mentioned in this respect it may relate to any other suitable substrate; the polymer top layer 20*a* is for separating (fluidics in the) at least one of the first micro-channel 11 and/or at least one of the first micro-chamber 12 embedded in the substrate (silicon) from (fluidics in the) at least one of the second micro-channel 21 and/or at least one of the second micro-chamber 22 embedded in the polymer bottom layer preferably at least partly by the matrix of holes 28 therein; the microfluidics of the polymer and silicon are directly or indirectly in microfluidic contact with one and another; the first micro-chamber (12) embedded in the substrate is accessible from the outside; in an example it may be regarded as a cavity, having a bottom and one or more side walls. The present polymer is independently selected from biocompatible polymers, such as polysiloxanes, such as polydimethylsiloxane (PDMS), polyimides, polyurethane, styrene-ethylene-butylene-styrene (SEBS), polypropylene, polycarbonate, polyester, polypropylene, and butyl rubber, and from biodegradable polymers, such as Biorubber (PGS), and poly(1,8-octanediol-co-citrate) (POC), and combinations thereof.

The term "fluidics" may relate to a gas, a liquid; and combinations thereof; a "microfluidic" is considered to be fluid under boundary conditions of the device.

The set-up composed by the polymer layers, typically forming a membrane or foil, the micro-channels, the micro-chambers, and first micro-chamber (also referred to as "macro-chamber") can be optically monitored off-line with a microscope and/or a camera e.g. placed on a backside/front-side of the device. The macro-chamber can have dimensions in the order of $100*100$ $\mu m^2$ to $10*10$ $mm^2$. The set-up can be monitored on-line by means of micro-electrode array and/or micro-fabricated sensors (such as flow/temperature/pH sensor) provided in the micro-environment and or in the macro-chambers. The set-up can be also altered/stimulated by means of liquid flow flowing through the micro-chamber/channels and the macro-chamber; likewise by gas flow flowing through the micro-chamber/channel and the macro-chamber; by pressure differences applied in the micro-chambers, in the micro-channels and on the backside and the front side of the membrane (see e.g. FIG. 11); by electrical stimulation provided by means of micro-electrode arrays; by optical stimulation provided with optical systems placed on the backside/front-side of the device; by chemical stimulation provided by means of liquid flow or liquid reservoir placed in the membrane; and other micro-fabricated actuators placed inside the micro-channel/chambers; and combinations thereof, hence the device is considered to be versatile.

The presented microchip is typically fabricated on a Silicon substrate with standard IC and MEMS technologies. The silicon bulk and the chosen fabrication process provide advantages such as: use of standard cleanroom compatible micro-fabrication processes to achieve wafer-scale fabrication that can be scaled up to volume production by eliminating manual assembly and sample handling. This enables high yield and throughput, thus, low cost volume production. The device can be equipped with additional modules embedded on the backside and/or front-side of the membrane and/or in the microenvironment composed by the micro-channels/chambers. By adding or removing one or more modules during fabrication, it is possible to adapt the device to meet different demands. Examples of the possible modules are: a micro-electrode array for electrical stimulation/monitoring of tissues in vitro cultured in the environment and or the gasses/liquid in the environment; a reference electrode for cell culture monitoring; Flow/temperature/pH sensors and or strain gauges for monitoring the environment in the micro-chamber/channels and/or macro-chambers; IC circuits such as pre-amplifiers for the signal detected by the sensors mentioned above; Microgrooves to promote cell alignment which grooves may be coated such as with an adhesive molecule and/or elastomer; micro-pillars to mix fluids; Micro-fabricated actuators such as hotplate to regulate environment temperature.

The present device can be used for various application including e.g. study of growth and differentiation of primary cells, such as human neuronal cells as well as any other cell requiring e.g. mechanical and/or electrical stimulations and also stratified structure; simulation of a microenvironment in a living tissue and/or organ.

The present device may find numerous applications in various Organ-on-Chips, Lab-on-Chips, microfluidics, and microreactors. The capability of the present device of having integrated electrical microstructures 29,90 allows to have cell micro-environments where real-time monitoring and stimulating of different types of cells is possible; e.g. electrical stimulation of heart cells or neurons, reading of neuron and heart cells electrical activity, trans-endothelial electrical resistance measurements in brain-blood barrier models, among other applications.

The present device also allows the control over the mechanical and topographical signals supplied to a cell microenvironment through its configurable polymeric layers, e.g. patterned surface 27, to improve adhesion and alignment of heart cells, flexible membrane layers 20*a,b* to apply stress on cultured cells locally, microporous surface 28 to allow and study migration of immune cells in lung and/or skin models, and study of the interface between two different cell cultures. Additionally, the device presents micro-features to precisely supply cell microenvironments with controlled fluid flows to allow air flow and/or blood flow in lung, liver, gut or brain barrier models, and cell microenvironment with different drugs and micro-chambers 22 that can be used as reservoirs for this drugs and/or any other biological or chemical agent. Therefore, the present device is adaptable to develop at least one of several organ-on-chip platforms such as Brain-on-Chip, Heart-on-Chip, Lung-on-Chip, Gut-on-Chip, Blood-Brain Barrier-on-chip, Liver-on-Chip and/or Kidney-on-Chip.

On the other hand, the inlets, micro-channels and micro-chambers of the present device may be used to develop microfluidics devices and/or micro-reactors either on a substrate to study biological processes and/or other phenomena requiring a precise control over the flow conditions in a micron and/or millimeter scale environment.

In a second aspect the present invention relates to a method of producing the present device. Therein e.g. a Si substrate 10 is provided and thereafter various more or less standard semiconductor process steps may be performed; first a first dielectric layer 51*a*, 51*b* is deposited/grown on both sides of the substrate, and thereafter the dielectric layer is patterned on a bottom side, i.e. on one side only; then depositing a first foil layer 61 of polymer material on the dielectric layer; the membrane layer is typically spun on the unpatterned Si-side of the dielectric layer, in an example PDMS is spun; thereafter a patterning step of the first membrane layer 61 is performed using optical lithography or electron beam lithography; it is considered quite atypical to use such patterning tools, as typically soft-lithographic process are used, that is "by hand"; in addition prior art processes are typically not fully integrated, such as being compatible with semiconductor processes; thereafter a sacrificial layer 72 is deposited on the first membrane layer, such as a dielectric layer or a photo resist (PR) layer; the PR may be provided by spinning; hereafter the first polymer membrane layer 61 is patterned using a lithography or electron beam machine; the first membrane polymer layer is etched with plasma etching/dry etching; typically an alignment step is involved for aligning microscopic/nanoscopic features; then a second membrane layer 62 is deposited on the sacrificial layer 72, such as by spinning; the second membrane layer may be of the same material (polymer) as the first membrane layer 61, or may be of a different material; then the Silicon substrate 10 is etched, preferably using dry etching, at the bottom side thereof, preferably stopping etch on the first dielectric layer, therewith providing openings for channels 11/chambers 12 in Si; the first dielectric layer 51*b* is then (wet) etched from the bottom side providing openings for channels/chambers; and as a further step the sacrificial layer 71 is then (wet) etched thereby releasing channels 21/chambers 22. The wafer may then be diced (cut) and mounted on an assembly including e.g. a well 35 for cell culturing, a microfluidic inlet 32, a pneumatic inlet 36 to stretch the membrane and an electrical output 18 to read the output of the electrodes, and the sensors embedded in the chip 38. The present method therewith provides a way of producing the present device.

In a third aspect the present invention relates to a use of the present device for at least one of a biological cell experiment, organ on a chip experiment, an optical microscope experiment, growth and differentiation of primary cell experiment, such as a human neuronal cell, mechanical and electrical stimulation of a cell, a stratified structure, simulation of a microenvironment in living tissue and/or organ, as Lab-on-Chip, as a microfluidics device, and as a microreactor; hence the present device may be considered to be very versatile.

It is noted that some of the steps may be performed in a different sequence, and/or at a later or earlier stage.

Thereby the present invention provides a solution to one or more of the above mentioned problems.

Advantages of the present invention are detailed throughout the description.

DETAILED DESCRIPTION OF THE INVENTION

The present invention relates in a first aspect to a device according to claim 1.

In an example the present device further comprises at least one of a microchip, an integrated sensor, and an output 18, such as embedded in the polymer based microfluidics and/or integrated and embedded in the substrate based microfluidics. The microchip may be fully integrated in the silicon 10, such as in a silicon substrate. The microchip may perform control functions and process input and provide (data) output. The output 18 may be located in the silicon and/or in the polymer; more than one output as well as more than one input may be present. The integrated sensor may be provided in the silicon and may be silicon based; the sensor is typically provided in a microfluidic channel/chamber. The sensor may relate to a chemical sensor, a physical sensor, etc.

In an example of the present device the polymer 20*a*-20*b* (foil) is stretchable having a tensile strength of >1 [MPa] (ISO 527) and/or flexible with a Young's modulus of <3 [GPa] (ISO 527), or wherein the membrane is rigid having a Young's modulus of >10 [GPa] (ISO 527).

In an example of the present device the polymer is independently selected from biocompatible polymers, such as poly-siloxanes, such as polydimethylsiloxane (PDMS), polyimides, polyurethane, styrene-ethylene-butylene-styrene (SEBS), polypropylene, polycarbonate, polyester, polypropylene, butyl rubber, ostemer, and biodegradable polymers, such as Biorubber (POS) and poly(1,8-octanediol-co-citrate) (POC), and combinations thereof. It may be an advantage to use a biodegradable material, as e.g. after initial culturing an interface between two cultures may gradually disappear. The polymer may be porous or non-porous, thereby having a certain permeability to fluids, such as determined by ISO 15105-1 or ISO 2556 for a gas and ISO 2528 for water.

In an example of the present device the polymer top layer (or membrane) comprises an array of nxm openings, wherein $n \in [1,10^6]$, preferably $n \in [2,10^5]$, more preferably $n \in [5,10^4]$, even more preferably $n \in [10,10^3]$, such as $n \in [100,500]$, wherein $m \in [1,10^6]$, preferably $m \in [2,10^5]$, more preferably $m \in [5,10^4]$, even more preferably $m \in [10, 10^3]$, such as $m \in [100,500]$, wherein a density of holes is 0.001-250/100 $\mu m^2$, preferably 0.01-100/100 $\mu m^2$, more preferably 0.1-50/100 $\mu m^2$, even more preferably 1-20/100 $\mu m^2$, and/or wherein an average hole area is 0.05-500 $\mu m^2$, preferably 0.1-200 $\mu m^2$, more preferably 0.2-100 $\mu m^2$, even more preferably 0.5-50 $\mu m^2$, such as 1-5 $\mu m^2$ or 10-30 $\mu m^2$.

In an example of the present device the polymer top layer (or membrane) comprises a plurality of interconnected hollow structures, such as a scaffold-like structure.

In an example the present device further comprises embedded in the device at least one of a sensor, a pump, a microelectrode, a valve, a strain gauge, an actuator, a heater, a cooler, a stimulator, a flow sensor, a temperature sensor, a pH sensor, an IC-circuit, an amplifier, an actuator, a hot plate, a micro-electrode array, a chemical stimulator, an optical stimulator, a pressure regulator, an ion sensor, and further elements. Such expresses the versatility of the present design and manufacturing method.

In an example the present device further comprises embedded in the thin polymer top layer 20*a* on least one electrode 29 and a microgroove, wherein the electrode preferably has an accessible area 29*a* of 0.2-5000 $\mu m^2$, preferably 0.25-2500 $\mu m^2$, more preferably 0.5-2000 $\mu m^2$, even more preferably 1-1000 $\mu m^2$, such as 2-500 $\mu m^2$ or 5-100 $\mu m^2$; the microgrooves may have a length between 0.4 to 5000 um, such as 1-500 um, a width between 0.4 to 5000, such as 1-50 um, and a depth between 0.2 and 50 $\mu m$, such as 1 to 20 um, e.g. 2-5 um.

In an example of the present device the thin polymer top layer 20*a* comprises on at least one side thereof, at least one micro-feature, such as an indentation, a groove, a topographical structure, preferably at least one oriented microgroove, preferably an array of x*y oriented microgrooves, wherein $x \in [1,10^6]$, preferably $x \in [2,10^5]$, more preferably $x \in [5,10^4]$, even more preferably $x \in [10,10^3]$, such as $x \in [100,500]$, wherein $y \in [1,10^6]$, preferably $y \in [2,10^5]$, more preferably $y \in [5,10^4]$, even more preferably $y \in [10,$ $10^3$], such as $y \in [100,500]$, wherein a density of micro-grooves is $10^{-4}$-25/100 µm², preferably $10^{-3}$-10/100 µm², more preferably $10^{-2}$-5/100 µm², and/or wherein an average groove area is 0.1-$10^6$ µm², preferably 1-$10^5$ µm², more preferably 10-$10^4$ µm², even more preferably 100-$10^3$ µm², such as 200-500 µm², and/or wherein a groove length is from 5 µm-5 mm, and/or wherein the at least one micro-feature is aligned with respect to an edge of the device or with respect to the first micro-chamber; the alignment may for instance be parallel to the edge or perpendicular thereto; the micro-features are typically aligned with respect to one and another as well, e.g. in a parallel fashion.

In an example of the present device at least one of the first micro-channel 11 and/or at least one of the first micro-chamber 12 embedded in the substrate (silicon) is accessible from the outside (i.e. "partly open"), and/or wherein the at least one of the first micro-channel 11 and/or at least one of the first micro-chamber 12 embedded in the substrate (silicon) have a height of 50-2000 µm, preferably 100-1000 µm, more preferably 200-500 µm, such as 300-400 µm; the micro-chamber 12 and the microchannel 11 may have various shapes, selected from circular, rectangular, hexagonal, oval, and multigonal; the microchannel may have an area of 20-$10^6$ µm², preferably 100-$10^5$ µm², more preferably 400-10000 µm²; the at least one of the second micro-channel 21 and/or at least one of the second micro-chamber 22 embedded in the polymer have a height of 1-1000 µm, preferably 50-500 µm, more preferably 100-400 µm, such as 200-300 µm.

In an example of the present device the first micro-channel 11 comprises at least one column made of polymer, which connects the top and the bot-tom side of the channel, preferably at least one oriented column, preferably an array of c*d columns 26, wherein $c \in [1,10^6]$, preferably $c \in [2, 10^5]$, more preferably $c \in [5,10^4]$, even more preferably $c \in [10,10^3]$, such as $c \in [100,500]$, wherein $d \in [1,10^6]$, preferably $d \in [2,10^5]$, more preferably $d \in [5,10^4]$, even more preferably $d \in [10,10^3]$, such as $d \in [100,500]$, wherein a density pillars is $10^{-4}$-25/100 µm², preferably $10^{-3}$-10/100 µm², more preferably $10^{-2}$-5/100 µm², and/or wherein a section area of a pillar is 1-$10^7$ µm², preferably 10-$10^6$ µm², more preferably 100-$10^5$ µm², even more preferably 1000-$5*10^4$ µm², such as 1000-$10^4$ µm².

In an example of the present device the walls of the micro-chamber 21 (cavity-like structure) and/or 12 may be coated with a conductive material 14, such as platinum, or with an electrically insulating material, such as parylene, or a combination of both. The platinum coating may be used as additional electrode directly in contact with the reservoir 35.

In an example of the present device the polymer layers 20a,20b are provided with openings, the openings providing access to at least one of a metal pad, an IC, a sensor, such as an optical sensor, a heater, etc.

In second aspect the present invention relates to a method according to claim 11 for making one or more devices, such as in a semiconductor process-like environment.

In an example of the present method the first 51a, b, and second 52 dielectric layers are made from a material independently selected from Si-dielectric materials, such as $SiO_2$, and $Si_3N_4$.

In an example of the present method a thickness of the first 51a,b and second 52 dielectric layer are each independently from 5-500 nm, preferably 10-250 nm, more preferably 20-100 nm, such as 30-50 nm.

In an example of the present method the flexible and or stretchable second and third dielectric layers 52,53 are made from a material independently selected from polymers such as polyamide and parylene.

In an example of the present method a thickness of the first foil layer 61 is from 50-30000 nm, preferably 250-5000 nm, more preferably 500-2000 nm, such as 1000-1500 nm.

In an example of the present method a thickness of the second foil layer 62 is from 50-2000 µm, preferably 200-1000 µm, more preferably 300-800 µm, such as 500-700 µm.

In an example of the present method the foil layers 61,62 are each independently made from a material selected from a biopolymer, preferably a biocompatible polymer, such as poly-siloxane, such as PDMS, polyimides, parylene, and biodegradable polymers, such as Biorubber (PGS) and poly (1,8-octanediol-co-citrate) (PCC), and combinations thereof.

In an example of the present method the sacrificial layer 72 is a photo resist, such as an I-line photo resist, silicon oxide, and a metal.

In an example of the present method patterning is performed using an I-line lithographic machine, such as an ASML PAS 5500.

In an example of the present method at least one dielectric layer is formed by one of PECVD, LPCVD, low-temperature PECVD, and thermal oxidation.

In an example of the present method dry etch of silicon is performed using DRIE and/or wherein wet etching of silicon is performed using KOH.

In an example of the present method at least one of the foil layers is spun.

In an example and/or partly in an alternative of the above method for making one or more devices, such as in a semiconductor process-like environment, the present method may comprise at least one step selected from;

providing a Si-substrate 10, optionally comprising at least one sensor 90, a microelectrode array 29, and at least two sets of micro-grooves 27, a1) depositing/growing a first dielectric layer 51a, 51b on at least one side of the substrate, and a2) patterning the dielectric layer on top and/or bottom side, i.e. on one of either sides or on both of the sides;

b1) depositing a metal layer on the top side of the substrate;

b2) patterning the metal layer;

c1) depositing the first flexible and/or stretchable dielectric layer on the top side of the substrate;

c2) patterning the first flexible and or stretchable dielectric layer;

d1) depositing a conductive layer such as metal and/or conductive polymers) on the top side of the substrate;

d2) patterning the conductive layer;

e1) depositing the second flexible and/or stretchable dielectric layer;

e2) patterning the second flexible and or stretchable dielectric layer;

f1) depositing the first sacrificial layer for the first set of micro-grooves;

f2) patterning the first sacrificial layer 71;

g) depositing a first foil layer 61 of the second dielectric layer; PDMS spinning on unpatterned Si-side h) patterning the first foil layer 61 using a lithography or electron beam machine;

i) partially etching the first membrane layer 61 using a lithography or electron beam machine for the second set of microgrooves j1) depositing a second sacrificial layer 72 on the first foil layer, such as PR, and PR spinning and j2) patterning the second sacrificial layer 72 using a lithography or electron beam machine;

k) depositing a second foil layer 62 on the sacrificial layer 72;

l) patterning the second foil layer 61;

m) dry or wet etching the Silicon substrate 10 at the bottom side, preferably stopping etch on the first dielectric layer, therewith providing openings for channels 11/chambers 12 in Si;

n1) deposition of a conductive and/or insulating chamber coating 14, such as platinum parylene; and optionally a chemical surface treatment, such as a hydrophilic treatment, n2) etching of the conductive or insulating chamber coating;

o) (wet) etching of the first dielectric layer 51b from the bottom side providing openings for channels/chambers; and p) (wet) etching of the sacrificial layer 72 thereby releasing channels 21/chambers 22.

In an example of the present method dimensions of the at least one first micro-channel 11 and/or at least one first micro-chamber 12 embedded in the substrate (silicon), the at least one input 16, the at least one second micro-channel 21 and/or at least one second micro-chamber 22 embedded in the polymer bottom layer, are each independently fully adaptable in a range of 50 nm-2 mm, and/or wherein the dimensions of the matrix of holes 28, the micro-features, are each independently fully adaptable in a range of 50 nm-100 µm, such as by lithography, such as by E-UV-I-line lithography and/or by e-beam lithography.

In an example of the present method the substrate layer comprises at least two alignment markers, and wherein during at least one method step the substrate 10 is aligned.

In a third aspect the present invention relates to a use according to claim 25.

In an example of the present use a wet/humid section and a dry section of the device are physically separated, wherein the dry section comprises electronics.

An example of the present use is as a blood-brain barrier model. The model may comprise brain microvascular endothelial cells (BMEC) and astrocytes cultured in the microchannel 21 or micro-chamber 22. These cells may be cultured on the silicon micro-chamber 12 together with neuron cells and/or other brain cells. The membrane layer 61 with a patterned surface 27 represents in such a case a dynamic interface that separates a central nervous system from a circulation system and as such creates a barrier. The microchannel 21 then allows to generate and supply shear stress to the barrier having effect on its permeability and function. The shear stress might be generated by blood or gas flowing through the microchannel 21 supplied by the silicon and polymer inlets in microfluidic contact 11,21. The electrical microstructures 21,14,90 make it possible to have an integrated trans-endothelial electrical measurement (TEER). The polymer membrane 20a,b also allows mechanical stimulation of the interface of the said cultured microenvironment.

In a fourth aspect the invention relates to an assembly comprising at least one of the present device 100, a reservoir 35 comprising a chip and a cylinder 31, a sealing on top of the device, a pressure chamber 34 comprising an inlet 36, an electrical input/output 38 connected to a printed circuit board (PCB) 39 with at least one electrical output 18, e.g. via flip chip connections or wire-bonding connections 37, for interfacing with e.g. an electrode 29 and/or a sensor 90.

The invention is further detailed by the accompanying figures and examples, which are exemplary and explanatory of nature and are not limiting the scope of the invention. To the person skilled in the art it may be clear that many variants, being obvious or not, may be conceivable falling within the scope of protection, defined by the present claims.

FIGURES

FIGS. 1a-p show details of an exemplary embodiment of the present method.

FIGS. 2a-2d, 3a-3b, 4-9, 10a-10c, 11a-11c, and 12 show exemplary details of the present device.

FIGS. 13-16 show examples of the present device and features thereof.

DETAILED DESCRIPTION OF THE FIGURES

In the figures:
100 microfluidic device
10 substrate
11 first micro-channel
12 first micro-chamber (macro-chamber)
14 coating layer
16 input
18 output
20a polymer top layer
20b polymer bottom layer
21 second micro-channel
21b isolated channel
21c channel, such as for drug delivery
22 second micro-chamber
26 (array of) columns
27 patterned structure
28 matrix of holes
28a single hole, such as for drug delivery
29 electrode
29a accessible area of electrode
31 cylinder
32 microfluidic inlet
34 pneumatic chamber
35 reservoir
36 pneumatic inlet
37 electrical connection
38 electrical input/output
39 printed circuit board
51a,51b first dielectric layer
52 second dielectric layer
53 third dielectric layer
61 first membrane polymer layer
62 second membrane polymer layer
71 first sacrificial layer
72 second sacrificial layer
81 contact pad
82 metal line and electrode
90 sensor FIGS. 1a-p show details of an exemplary embodiment of the present method. The method includes fabrication of a microelectrade array, an array of columns in the channel, two set of microgrooves, and an embedded sensor/electrode in the Silicon support.

FIG. 1a shows provision of a silicon substrate and Silicon Oxide deposition (front and back) and patterning (on Silicon wafer with integrated sensor)

FIG. 1b shows Aluminum deposition and patterning (for contact pads)

FIG. 1c shows First isolation layer (such as parylene/polymide) deposition and patterning FIG. 1d shows Metal deposition and patterning (for metal lines and electrodes)

FIG. 1e shows Second isolation layer (such as parylene/polymide) deposition and patterning FIG. 1f shows Spinning and patterning of sacrificial layer (for first set of Micro-grooves)

FIG. 1g shows PDMS spinning

FIG. 1h shows PDMS patterning (landing on wafer)

FIG. 1i shows PDMS patterning (partial etching—second set of grooves)

FIG. 1j shows sacrificial layer deposition and patterning (for channels); k) Second PDMS layer spinning; l) Second PDMS layer patterning; m) Silicon etching; n) Macro-chamber coating (platinum/parylene); o) Silicon oxide etching; and p) Micro-chamber/channels releasing and first set of grooves releasing.

Figure 12:
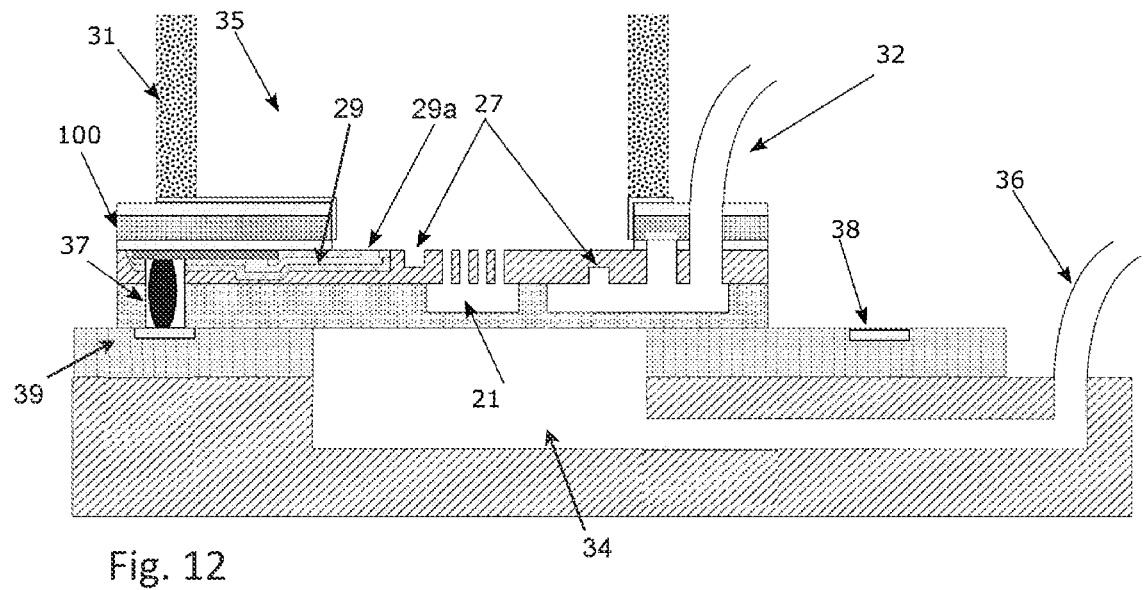

FIG. 2a,b,c,d show details of an exemplary embodiment of one device that includes one channel 21 accessible through an inlet and an outlet 16 and through hole matrix 28 in the micro-chamber 12.

FIGS. 3a and 3b show respectively details of an exemplary embodiment of two devices equipped with a micro-channel 21 and a micro-chamber 22 respectively embedded in the polymer layers 20a,b.

FIG. 4 shows details of an exemplary embodiment of a device equipped with an array of electrodes embedded in the top polymer layer 20a.

FIG. 5 shows details of an exemplary embodiment of a device with an etched hole in the top polymer layer 20a that expose the sensor/electrode 90 with the solution in channel 21.

FIG. 6 shows details of an exemplary embodiment of a device with an opening on the top and bottom polymer layer than can be used as electrical input/output for the electrodes and/or sensors 28,90 and layer 14.

FIG. 7 shows details of an exemplary embodiment of a device equipped with an array of microgrooves to promote the alignment of the cell culture in the reservoir 35.

FIG. 8 shows details of an exemplary embodiment of a device equipped with an array of columns 26 connecting the two polymer layer 20a,20b separated by a microchamber 21 and or a microchannel 22.

FIG. 9 shows details of an exemplary embodiment of a device equipped with a coating layer 14 deposited on the walls of the microchamber 12. This may be used as reference electrode in case of a conductive coating layer such as platinum or as an electrical isolation from the cell culture in case of an isolating layer such as parylene or polyamide.

FIGS. 10a,b,c, show details of an exemplary embodiment of one device that includes three independent channels 21 accessible through four inlets 16 and via hole matrix 28 in the micro-chamber 12. One of the channel 21a is connected to two inlet and may be used for 3D cell culturing. Channel 21c is connected to chamber 12 via a single hole 28a and may be used to deliver drugs to the cell culture. Channel 21b is isolated and can be used to locally stretch the cell culture in 12 by applying a difference in pressure between the channel 21c and the micro-chamber 12.

FIG. 11 shows details of an exemplary embodiment of one device when it is in relaxed state (FIG. 11a), when the polymer layers are stretched by applying a difference of pressure between the microchamber 12 and the back of the thick polymer layer 20b (FIG. 11b), when the thin polymer layer is locally stretched by applying a difference of pressure between the microchamber 12 and the microchannel 21 (FIG. 11c).

FIG. 12 shows details of an exemplary embodiment of one device mounted in an assembly composed by or more device 100, one or more reservoir 35 composed by the chip and a cylinder 31 sealed on top of the device 100, one or more microfluidic inlet 32 to impose a flow in the channel 21, one or more pressure chamber 34 comprising an inlet 36 and one or more electrical input/output 38 placed on a printed circuit board 39 connected to the device electrical output 18 via flip chip connections or wire-bonding connections 37, in order to interface with the electrodes 29 and or the sensors 90 embedded in the device 100.

Figure 13:
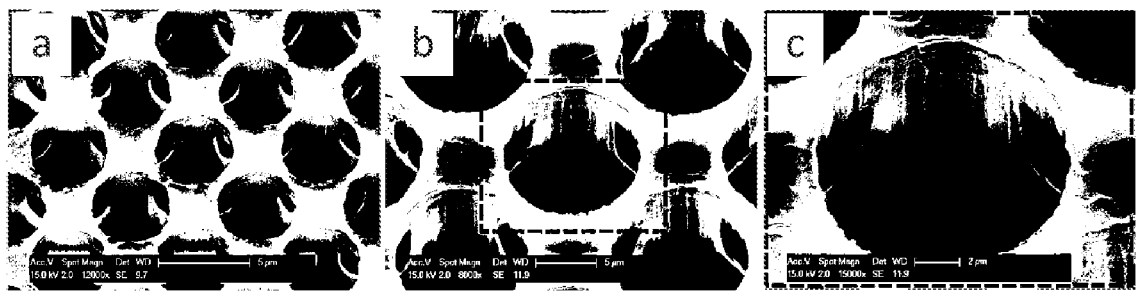

FIGS. 13a-c show an example of openings 28 etched in thin polymer top layer 20a. The holes have a circular shape and a width of about 5 µm (FIG. 13a) and about 7 µm (FIGS. 13b-c), and a depth of about 5 µm. The holes are interconnected through the foil by passages of which a few are indicated with arrows. As such a very open scaffold type foil is formed, such as comprising a plurality of interconnected hollow structures.

Figure 14:
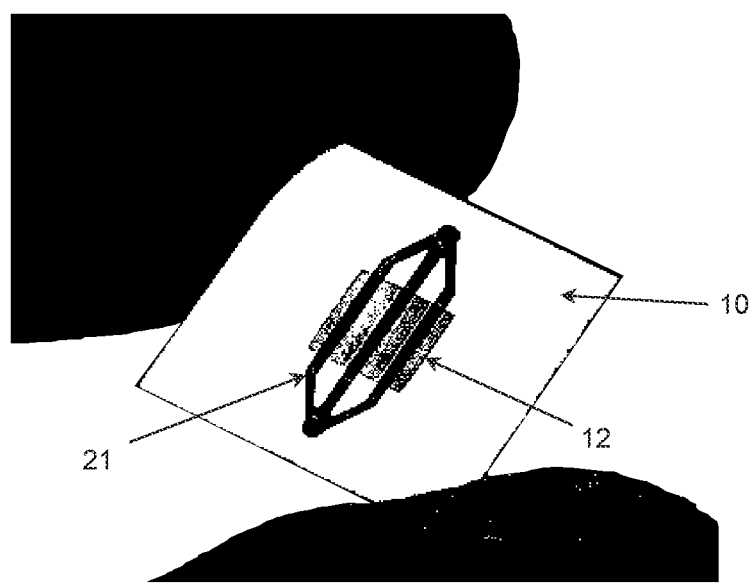
Figure 15:
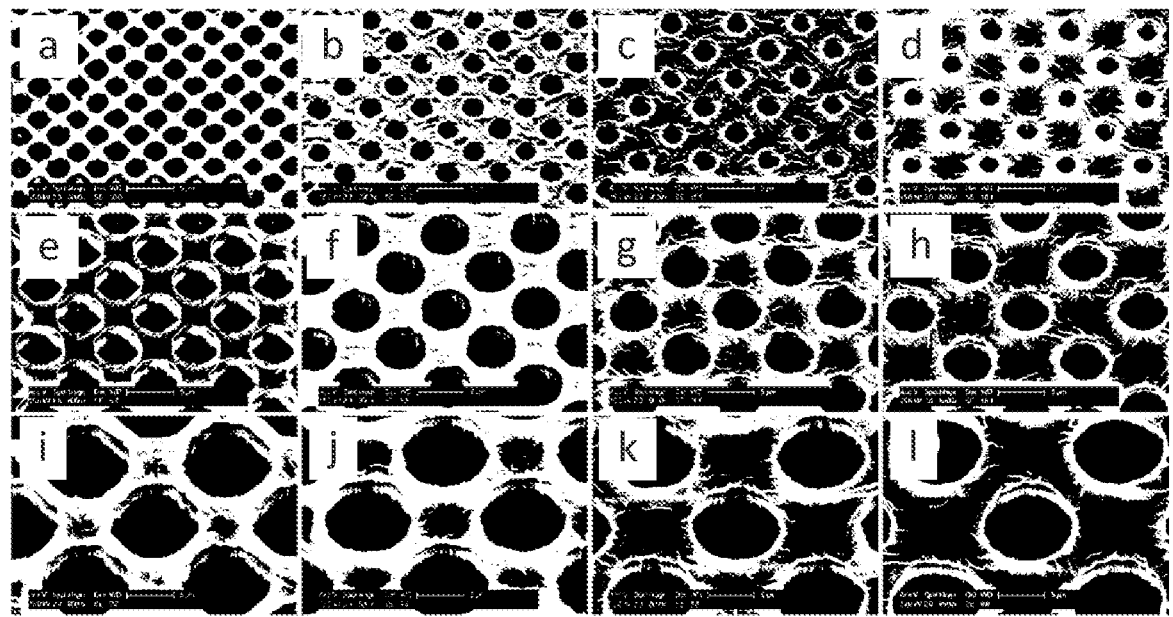

FIG. 14 shows an example of the present device held by a thumb and a finger. Therein substrate based microfluidics 10, first micro-chamber (macro-chamber) 12, which macro-chamber may be a cavity, and second micro-channel 21 can be seen.

FIGS. 15a-l show examples of size and pore-pore distance variations being possible with the present device. The top row has a pore size of 1 µm, the middle row of 2.5 µm and the bottom row of 5 µm. The left column has a pore-pore distance of 1 µm, the second row of 2 µm, the third row of 3 µm, and the right row of 4 µm.

Figure 16:
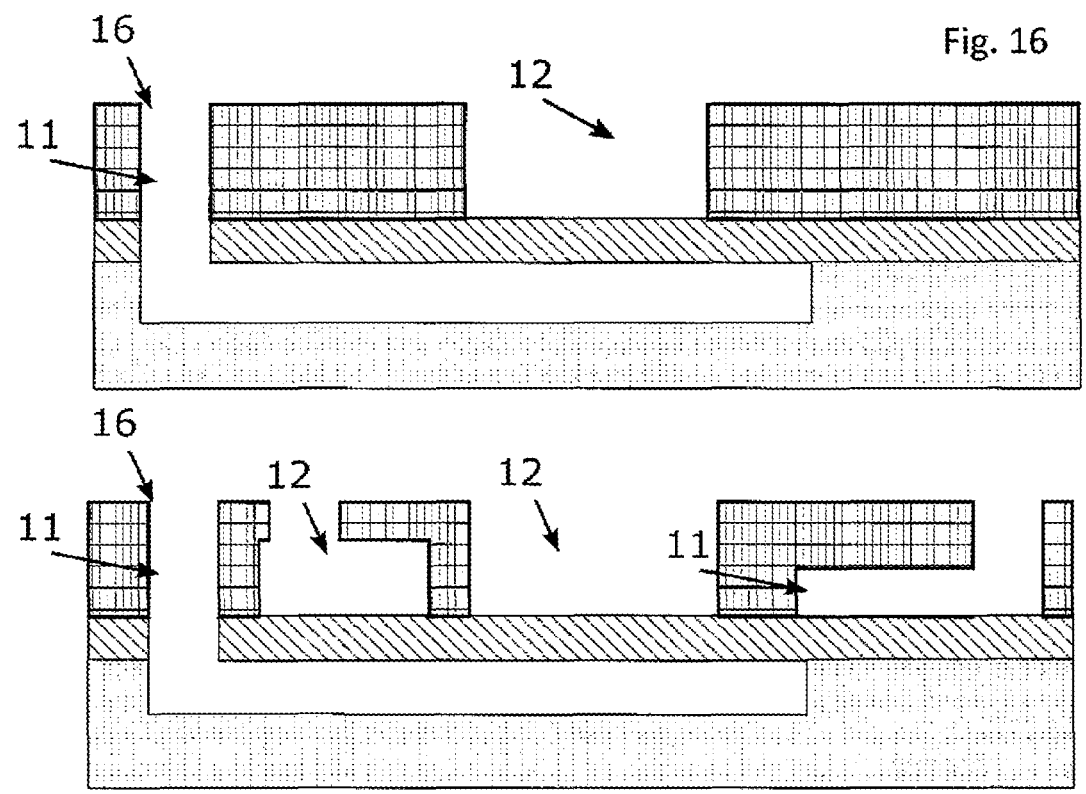

FIG. 16 shows two examples of the present device. In the top example in the substrate 10 microfluidics are provided. A first micro-channel 11, a first micro-chamber (macro-chamber) 12, which macro-chamber may be considered as a cavity (here and throughout the description as well) and an input 16 are provided. The height of the substrate is about 500 µm. In the polymer layer only one horizontal micro-channel 21 is shown. In the bottom example even less elements are provided. A width of the channel 21 is from 1-5 cm.

EXAMPLES/EXPERIMENTS

The invention although described in detailed explanatory context may be best understood in conjunction with the accompanying examples and figures.

The invention claimed is:

1. A microfluidic device comprising:
an optically transparent film composed of a first polymer layer having a thickness in a range of 0.05 µm to 30 µm and a second polymer layer having a further thickness in a range of 50 µm to 2000 µm;
a substrate defining a first surface and a second surface on opposite sides of the substrate, said first surface forming an upper surface of the microfluidic device in the operational position, and wherein the first polymer layer is sandwiched between the second polymer layer and the substrate and contacts the second surface of the substrate;
a first microfluidic chamber formed as a well in the substrate, the well extending vertically down into the substrate and from an access opening provided in the first surface of the substrate, and wherein the well is surrounded from lateral directions by inner peripheral walls defined by the substrate, wherein the well is bounded from below by an exposed portion of the first polymer layer that is not covered by the substrate, and wherein the well is not covered in vertical direction by the substrate but opens directly into the access opening, such that the well and the exposed portion of the first polymer layer are directly accessible from above via the access opening;

at least one of a second microfluidic channel and a second microfluidic chamber embedded in the second polymer layer and extending below the first polymer layer, below the first microfluidic chamber, and below the access opening in the first surface of the substrate, wherein the exposed portion of the first polymer layer includes a matrix of through-holes and forms a selective barrier between the first microchamber and the least one of the second microchannel and the second microchamber, and a first microfluidic channel, separate from the well and extending entirely through the substrate, from an aperture that is provided in the first surface of the substrate but separate from the access opening of the well, to a further aperture provided in the second surface of the substrate and in the first polymer layer, said further aperture opening into at least one of the second microfluidic channel and the second microfluidic chamber, such that the aperture is via the first microfluidic channel in fluid connection with the at least one of the second microfluidic channel and the second microfluidic chamber.

2. The microfluidic device according to claim 1, wherein the first and second polymer layers consist essentially of a polymer that is independently selected from biocompatible polymers, polyimides, polyurethane, butyl rubber, styrene-ethylene-butylene-styrene (SEBS), polypropylene, polycarbonate, polyester, off-stoichiometry thiol-ene polymer (ostemer), and biodegradable polymers, and combinations thereof.

3. The microfluidic device according to claim 1, wherein a holes-per-area density of the matrix of through-holes is 0.001-250/100 $\mu m^2$, and wherein an average hole area is 0.05-500 $\mu m^2$.

4. The microfluidic device according to claim 1, further comprising embedded in the device at least one of a sensor, a pump, a valve, a strain gauge, a heater, a cooler, a stimulator, a flow sensor, a temperature sensor, a pH sensor, an IC-circuit, an amplifier, an actuator, a hot plate, a chemical stimulator, an optical stimulator, an ion sensor, and a pressure regulator.

5. The microfluidic device according to claim 1, wherein the first polymer layer comprises, on the exposed portion of the first polymer layer facing the first microfluidic chamber a microgroove array, the microgroove array extending inside the first microfluidic chamber and being located above and alongside a lateral edge of the second microfluidic channel, wherein a grooves-per-area density of the microgroove array is 1-25/100 $\mu m^2$, wherein an average groove area is 0.1-$10^6$ $\mu m^2$.

6. The microfluidic device according to claim 1, wherein at least one of the at least one first micro-channel and at least one first micro-chamber embedded in the substrate have a height of 50-2000 $\mu m$ and the first micro-chamber having horizontal dimensions from 100*100 $\mu m^2$ to 10*10 $mm^2$, at least one of the second micro-channel and at least one of the second micro-chamber embedded in the second polymer layer have a height of 1-1000 $\mu m$.

7. The microfluidic device according to claim 1, wherein the first and second polymer layers are provided with openings, the openings providing access to at least one of a metal pad, an IC, a sensor, and a heater.

8. The microfluidic device according to claim 1, for use in at least one of a biological cell experiment, an organ on a chip experiment, an optical microscope experiment, growth and differentiation of primary cell experiment, mechanical and electrical stimulation of a cell, a stratified structure, simulation of a microenvironment in living tissue and organ, as Lab-on-Chip, and as a micro-reactor.

9. The microfluidic device according to claim 1, wherein the first and second polymer layers consist essentially of a polymer that is at least one of stretchable having a tensile strength of >1 [MPa] (ISO 527), flexible with a Young's modulus of <3 [GPa] (ISO 527), and rigid having a Young's modulus of >10 [GPa] (ISO 527).

10. The microfluidic device according to claim 1, further comprising a microelectrode embedded in the first polymer layer, wherein the microelectrode includes a sensing area provided at the exposed portion of the first polymer layer and facing the first microfluidic chamber;
wherein the microelectrode extends in a lateral direction within the first polymer layer, thereby connecting the sensing area of the microelectrode with an electrical output connection provided at a further portion of the first polymer layer, said further portion being covered by the substrate and remote from the first microfluidic chamber.

11. The microfluidic device according to claim 10, wherein the microelectrode is a microelectrode array defining a plurality of sensing areas provided along the exposed portion of the first polymer layer and facing the first microfluidic chamber, wherein the sensing areas are arranged in a sequence alongside a lateral edge of the matrix of through-holes provided in the exposed portion of the first polymer layer.

12. The microfluidic device according to claim 1, wherein the substrate is silicon or dielectric on silicon.

13. The microfluidic device according to claim 1, wherein the microfluidic device is a microchip.

14. The microfluidic device according to claim 1, wherein the second micro-chamber comprises at least one column made of polymer, the at least one column connecting a top side of the second microchamber with a bottom side of the microchamber.

15. A microfluidic device comprising:
an optically transparent film composed of a first polymer layer having a thickness in a range of 0.05 $\mu m$ to 30 $\mu m$ and a second polymer layer having a further thickness in a range of 50 $\mu m$ to 2000 $\mu m$;
a substrate defining a first surface and a second surface on opposite sides of the substrate, said first surface forming an upper surface of the microfluidic device in the operational position, and wherein the first polymer layer is sandwiched between the second polymer layer and the substrate and contacts the second surface of the substrate;
a first microfluidic chamber formed as a cavity in the substrate, the cavity being enclosed from lateral directions by the substrate, the cavity being bounded from below by an exposed portion of the first polymer layer that is not covered by the substrate, and the cavity being open from above via an access opening provided in the first surface of the substrate, such that the cavity and the exposed portion of the first polymer layer are directly accessible from above via the access opening;

at least one of a second microfluidic channel and a second microfluidic chamber embedded in the second polymer layer and extending below the first polymer layer and the first microfluidic chamber, wherein the exposed portion of the first polymer layer includes a matrix of through-holes and forms a selective barrier between the first microchamber and the least one of the second microchannel and the second microchamber, and a first microfluidic channel, extending entirely through the substrate, thereby connecting an aperture provided in the first surface of the substrate with a further aperture provided in the second surface of the substrate and in the first polymer layer such that the aperture is via the first microfluidic channel in fluid connection with the at least one of the second microfluidic channel and the second microfluidic chamber, a microelectrode embedded in the first polymer layer, wherein the microelectrode includes a sensing area provided at the exposed portion of the first polymer layer and facing the first microfluidic chamber, wherein the microelectrode extends in a lateral direction within the first polymer layer, thereby connecting the sensing area of the microelectrode with an electrical output connection provided at a further portion of the first polymer layer, said further portion being covered by the substrate and remote from the first microfluidic chamber.

16. The microfluidic device according to claim 15, wherein the microelectrode is a microelectrode array defining a plurality of sensing areas provided along the exposed portion of the first polymer layer and facing the first microfluidic chamber, wherein the sensing areas are arranged in a sequence alongside a lateral edge of the matrix of through-holes provided in the exposed portion of the first polymer layer.

17. The microfluidic device according to claim 15, wherein the first and second polymer layers consist essentially of a polymer that is independently selected from biocompatible polymers, polyimides, polyurethane, butyl rubber, styrene-ethylene-butylene-styrene (SEBS), polypropylene, polycarbonate, polyester, off-stoichiometry thiol-ene polymer (ostemer), and biodegradable polymers, and combinations thereof.

18. The microfluidic device according to claim 15, wherein the substrate is silicon or dielectric on silicon.

19. The microfluidic device according to claim 15, wherein the microfluidic device is a microchip.

20. The microfluidic device according to claim 15, wherein the first polymer layer comprises a microgroove array on the exposed portion of the first polymer layer facing the first microfluidic chamber, the microgroove array extending inside the first microfluidic chamber and being located above and alongside a lateral edge of the second microfluidic channel.

* * * * *